(12) United States Patent
Ham et al.

(10) Patent No.: US 11,273,192 B2
(45) Date of Patent: Mar. 15, 2022

(54) METHOD OF PRODUCING GINSENG LEAF EXTRACT INCLUDING GINSENOSIDES RG6, RK3, AND RH4 IN INCREASED AMOUNTS FROM GINSENG LEAF AND USE OF THE GINSENG LEAF EXTRACT

(71) Applicant: KOREA INSTITUTE OF SCIENCE AND TECHNOLOGY, Seoul (KR)

(72) Inventors: Jungyeob Ham, Gangneung-si (KR); Taejung Kim, Gangneung-si (KR); Young Tae Park, Gangneung-si (KR); Kyusun Kim, Gangneung-si (KR); Pilju Choi, Gangneung-si (KR); Seon-Jun Choi, Gangneung-si (KR); Bong Geun Song, Gangneung-si (KR); Jae Young Choi, Seoul (KR)

(73) Assignee: KOREA INSTITUTE OF SCIENCE AND TECHNOLOGY, Seoul (KR)

(*) Notice: Subject to any disclaimer, the term of this patent is extended or adjusted under 35 U.S.C. 154(b) by 300 days.

(21) Appl. No.: 16/428,626

(22) Filed: May 31, 2019

(65) Prior Publication Data
US 2019/0365838 A1     Dec. 5, 2019

(30) Foreign Application Priority Data

Jun. 1, 2018  (KR) .......................... 10-2018-0063527

(51) Int. Cl.
| | | |
|---|---|---|
| *A61K 36/258* | (2006.01) | |
| *A23L 33/105* | (2016.01) | |
| *A61K 8/9789* | (2017.01) | |
| *A61K 31/704* | (2006.01) | |
| *A61Q 19/08* | (2006.01) | |
| *A61K 8/63* | (2006.01) | |

(52) U.S. Cl.
CPC .......... *A61K 36/258* (2013.01); *A23L 33/105* (2016.08); *A61K 8/9789* (2017.08); *A61K 31/704* (2013.01); *A61Q 19/08* (2013.01); *A23V 2002/00* (2013.01); *A23V 2200/318* (2013.01); *A23V 2250/2124* (2013.01); *A61K 2236/30* (2013.01)

(58) Field of Classification Search
CPC .. A61K 36/258; A61K 8/9789; A61K 31/704; A61K 2236/30; A61K 8/63; A23L 33/105; A61Q 19/08; A23V 2002/00; A23V 2250/2124; A23V 2200/318
See application file for complete search history.

(56) References Cited

FOREIGN PATENT DOCUMENTS

| | | |
|---|---|---|
| EP | 2 854 828 B1 | 8/2019 |
| KR | 10-2013-0132264 A | 2/2013 |

OTHER PUBLICATIONS

Park et al, Increase in apoptotic effect of Panax ginseng by microwave processing in human prostate cancer cells: in vitro and in vivo studies, 2016, J Ginseng Res, 40, pp. 62-67. (Year: 2016).*

(Continued)

*Primary Examiner* — Trevor Love
(74) *Attorney, Agent, or Firm* — Birch, Stewart, Kolasch & Birch, LLP

(57) ABSTRACT

Provided are a method of efficiently producing a ginseng leaf extract including rare ginsenosides Rg6, Rk3, and Rh4 in increased amounts, and use of a ginseng leaf extract produced by the method.

5 Claims, 12 Drawing Sheets

(56) References Cited

OTHER PUBLICATIONS

"Don't throw away Ginseng Leaves: Yield to your skin." Union Reporter, Dec. 9, 2012.
Office Action dated Jun. 24, 2019, in Korean Patent Application No. 10-2018-0063527.
Shi et al., "Investigation of ginsenosides in different parts and ages of *Panax ginseng*," Food Chemistry (2007), vol. 102, pp. 664-668.
Shin et al., "Chemical diversity of ginseng saponins from Panax ginseng", Journal of Ginseng Research, 39, 287-298, (2015).

* cited by examiner

METHOD OF PRODUCING GINSENG LEAF EXTRACT INCLUDING GINSENOSIDES RG6, RK3, AND RH4 IN INCREASED AMOUNTS FROM GINSENG LEAF AND USE OF THE GINSENG LEAF EXTRACT

CROSS-REFERENCE TO RELATED APPLICATION

This application claims the benefit of Korean Patent Application No. 10-2018-0063527, filed on Jun. 1, 2018, in the Korean Intellectual Property Office, the disclosure of which is incorporated herein in its entirety by reference.

BACKGROUND

Field

One or more embodiments relate to a ginseng leaf extract including ginsenosides Rg6, Rk3, and Rh4 in increased amounts through microwave processing and a method of producing the ginseng leaf extract.

Description of the Related Art

*Panax ginseng*, the ginseng species, is a herbaceous perennial plant that is native to the mountains of Northeast Asia, and is classified under the genus *Panax* of the family Araliaceae. The genus *Panax* also includes *Panax quinquefolius* native to North America, *Panax trifolius, Panax notoginseng* from Yunnan province in China, *Panax pseudoginseng*, and the like. These species show distinct differences in the shapes of their roots, stems, and leaves, and have large differences between regions in terms of component compositions and amounts thereof (*J Ginseng Res,* 39, 287-298, 2015).

Until now, ginseng research has mainly been concentrated on the roots while little research has yet been conducted on stems, leaves, and fruits other than roots. In particular, ginseng leaves have not proved to be economically useful, and thus are mostly discarded when the ginseng roots are harvested.

Ginsenosides, which are also called ginseng saponins, are a major component in terms of ginseng efficacy, and are present in the form of triterpene glycosides that are mainly composed of dammarane-based non-glycosides and several different saccharides. About 40 kinds of ginsenosides are known to date, and each of the different ginsenoside components included in ginseng has been reported to have a variety of medicinal effects.

Ginsenosides Rg6, Rk3, and Rh4 are compounds represented by Formulae 1 to 3, respectively, wherein ginsenosides Rk3 and Rh4 have an isomeric relationship with each other:

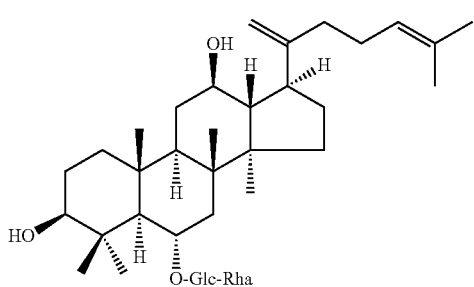

(Formula 1)

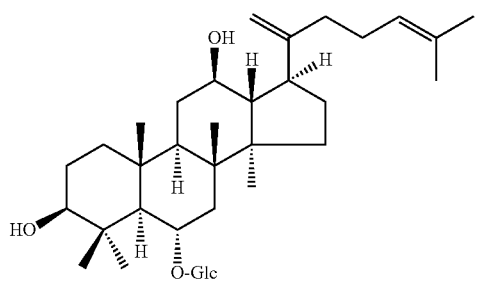

(Formula 2)

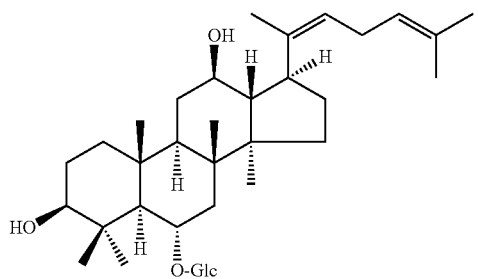

(Formula 3)

In this regard, there is a demand for a method of efficiently producing a ginseng extract including rare ginsenosides Rg6, Rk3, and Rh4 in increased amounts and use of the ginseng extract produced by the method.

SUMMARY

One or more embodiments include a method of producing an *Panax* genus plant extract, the method including performing microwave irradiation of leaves of a plant in the *Panax* genus or an extract of the leaves, wherein the *Panax* genus plant extract includes rare ginsenosides Rg6, Rk3, and Rh4 at a weight of 20% or more with respect to the weight of total ginsenosides obtained, and the total ginsenosides include Rg1, Re, Rh1, Rg2, Rb1, Rc, Rb2, Rd, Rg6, Rk3, Rh4, F2, S-Rg3, R-Rg3, Rk1, C-Y, C-K, Rk1, Rg5, Rh2, Rrk2, and Rh3.

One or more embodiments include a *Panax* genus plant extract produced by the method.

One or more embodiments include a pharmaceutical composition including the *Panax* genus plant extract produced by the method.

One or more embodiments include a composition for food, the composition including the *Panax* genus plant extract produced by the method.

One or more embodiments include a cosmetic composition for improving skin wrinkles, the cosmetic composition including the *Panax* genus plant extract produced by the method.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Figure 1:
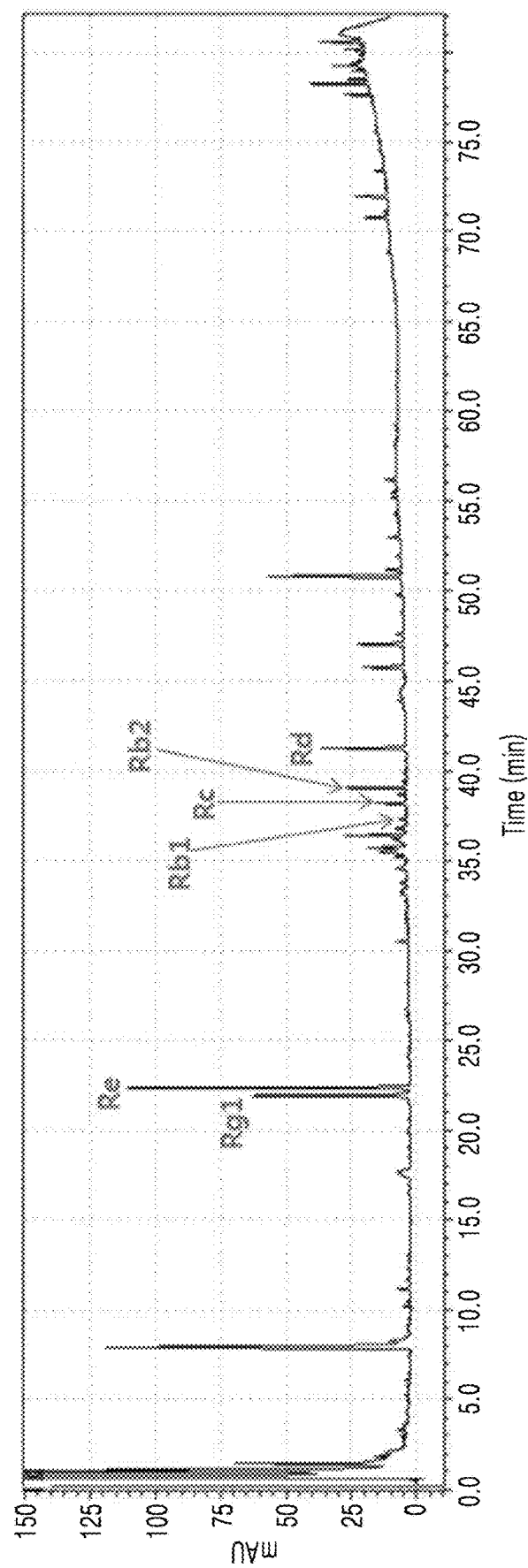
FIG. 1 is an ultra-performance liquid chromatography (UPLC) chromatogram of ginsenoside components of a raw ginseng leaf extract.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description.

Additional aspects will be set forth in part in the description which follows and, in part, will be apparent from the description, or may be learned by practice of the presented embodiments.

An aspect of the present disclosure provides a method of producing an extract of plants in the genus *Panax*, the method including performing microwave irradiation on a leaf of plants in the genus *Panax* or an extract of the leaf, wherein the extract includes rare ginsenosides Rg6, Rk3, and Rh4 at a weight of 20% or more with respect to the total ginsenoside weight, and the total ginsenoside includes Rg1, Re, Rh1, Rg2, Rb1, Rc, Rb2, Rd, Rg6, Rk3, Rh4, S-Rg3, R-Rg3, Rk1, and Rg5.

In one embodiment regarding the method, the weight of the rare ginsenosides with respect to the total ginsenoside may be about 20% or more, about 25% or more, about 30% or more, about 35% or more, about 40% or more, about 45% or more, about 50% or more, about 55% or more, about 60% or more, about 65% or more, about 70% or more, about 75% or more, about 80% or more, about 85% or more, about 90% or more, about 20 to about 95%, about 30 to about 95%, about 40 to about 95%, about 50 to about 95%, about 60 to about 95%, about 70 to about 95%, or about 70% to about 95%.

The extract of plants in the genus *Panax* produced by the method may include: Rg6 at a weight of about 4.5% or more, for example, about 4.5% to about 20%, about 4.5% to about 16%, about 5.0% to about 20%, about 5.0% to about 16%, about 6.0% to about 16%, about 7.0% to about 16%, about 8.0% to about 16%, about 9.0% to about 16%, or about 10.0% to about 16%, with respect to the total ginsenoside weight, Rk3 at a weight of about 2.0% or more, for example, about 2.0% to about 32.0%, about 5.0% to about 32.0%, about 8.0% to about 32.0%, about 11.0% to about 32.0%, about 13.0% to about 32.0%, or about 14.0% to about 32.0%, with respect to the total ginsenoside weight; Rh4 at a weight of about 2.5% or more, for example, about 2.5% to about 47.5%, about 5.0% to about 47.5%, about 7.5% to about 47.5%, about 10.0% to about 47.5%, about 14.0% to about 47.5%, about 20.0% to about 47.5%, about 30.0% to about 47.5%, or about 40.0% to about 47.5%, with respect to the total ginsenoside weight; or a combination thereof. The extract of plants in the genus *Panax* produced by the method may include Rg6:Rk3:Rh4 at an amount ratio of 5 to 16:7 to 32:8.0 to 48. The extract of plants in the genus *Panax* produced by the method may be extracted by using a solvent, and thus may not be fractionated.

The plants in the genus *Panax* may include *Panax ginseng, Panax quinquefolius, Panax notoginseng, Panax japonica, Panax trifolius, Panax pseudoginseng, Panax vietnamensis*, or a combination thereof. A leaf of the plants in the genus *Panax* may be the one at any time during the growth and development period. For example, the leaf may be the one at 30 to 120 days after the growth and development period. The leaf may be the one available before the ginseng is harvested from a germination leaf of the ginseng.

The ginseng leaf may include ginsenosides Rg1 and Re. The ginseng leaf may include, for example, ginsenosides Rg1, Re, Rb1, Rc, Rb2, and Rd.

The microwave irradiation may be performed on a liquid medium containing the leaf of plants or the extract of the leaf. The liquid medium may contain water, $C_1$-$C_6$ alcohol, or a mixture thereof. $C_1$-$C_6$ alcohol may include methanol, ethanol, propanol, butanol, pentanol, or hexanol. The mixture of water and $C_1$-$C_6$ alcohol may be a mixture of water and methanol, a mixture of water and ethanol, a mixture of water and propanol, a mixture of water and butanol, a mixture of water and pentanol, or a mixture of water and hexanol. Such a mixture may contain methanol, ethanol, propanol, butanol, pentanol, or hexanol at a weight in a range of about 30% to about 100%, about 30% to about 80%, about 30% to about 60%, about 40% to about 60%, or about 45% to about 55%, in water.

In one embodiment regarding the method, the term "the extract of the leaves" used in the expression "the leaves of a plant in the genes *Panax* and the extract of the leaf" may include ginsenosides Rg1 and Re at a weight of about 55% or more with respect to the total ginsenoside weight. "The extract of the leaf" may include Rg1 and Re at a weight of about 55% or more with respect to the total ginsenoside weight. "The extract of the leaf" may include an extract of the leaves of a plant in the genus *Panax* in water, a $C_1$-$C_6$ alcohol, or a mixture of water and $C_1$-$C_6$ alcohol. "The extract of the leaf" may be obtained by performing an extraction process by contacting a solvent with the leaves of a plant in the genus *Panax*. The "extract of the leaf" may be obtained according to a method including contacting with water, a $C_1$-$C_6$ alcohol, or a mixture thereof.

In one or more embodiments regarding the method, the microwave irradiation refers to a thermal reaction in which the extract of the ginseng leaf is heated by performing microwave irradiation thereon. Microwaves used in the microwave irradiation may have a main frequency of about 300 MHz to about 300 GHz, for example, about 1,000 MHz to about 100 GHz, about 1,000 MHz to about 50 GHz, about 1,000 MHz to about 10 GHz, or about 1,000 MHz to about 5 GHz.

Conditions for the microwave irradiation are not particularly limited, and may include any reaction condition resulting the inclusion of ginsenosides Rg6, Rk3, and Rh4 at a weight of 20% or more with respect to the total ginsenoside weight by the microwave irradiation. A resulting product by the microwave irradiation may be used as it is, but may be contained in the form of a dried product or a lyophilized product.

The microwave irradiation may be performed at pH 5.0 to 7.0, pH 5.0 to 6.0, or pH 6.0 to 7.0. The microwave irradiation may be performed on a neutral solution, for example, an aqueous solution. The aqueous solution may be water, $C_1$-$C_6$ alcohol, or a mixture thereof. $C_1$-$C_6$ alcohol may include methanol, ethanol, propanol, butanol, pentanol, or hexanol. The mixture of water and $C_1$-$C_6$ alcohol may be a mixture of water and methanol, a mixture of water and ethanol, a mixture of water and propanol, a mixture of water and butanol, a mixture of water and pentanol, or a mixture of water and hexanol. Such a mixture may contain methanol, ethanol, propanol, butanol, pentanol, or hexanol at a weight in a range of about 30% to about 100%, about 30% to about 80%, about 30% to about 60%, about 40% to about 60%, or about 45% to about 55%, in water. The output of microwaves is not particularly limited, and may be appropriately increased or decreased according to an amount of a reactant. For example, microwaves having power of 50 W to 1,000 W, for example, 100 W to 700 W may be used.

The microwave irradiation may be performed under pressure, for example, at a pressure of about 1 atm to about 100 atm, about 2 atm to about 100 atm, about 5 atm to about 100 atm, about 7 atm to about 100 atm, about 10 atm to about 100 atm, about 15 atm to about 100 atm, about 1.5 atm to about 80 atm, about 2 atm to about 80 atm, about 5 atm to about 80 atm, about 7 atm to about 80 atm, about 10 atm to about 80 atm, about 15 atm to about 80 atm, about 1.5 atm to about 50 atm, about 2 atm to about 50 atm, about 5 atm to about 50 atm, about 7 atm to about 50 atm, about 10 atm to about 50 atm, about 15 atm to about 50 atm, about 1.5 atm to about 30 atm, about 2 atm to about 30 atm, about 7 atm to about 50 atm, about 10 atm to about 50 atm, about 1.5 atm to about 30 atm, about 2 atm to about 30 atm, about 5 atm to about 30 atm, about 7 atm to about 30 atm, about 10 atm to about 30 atm, or about 15 atm to about 30 atm.

The microwave irradiation may be performed at a temperature of about 110° C. to about 150° C., for example, about 110° C. to about 140° C., about 110° C. to about 130° C., about 110° C. to about 120° C., about 120° C. to about 150° C., about 120° C. to about 140° C., about 120° C. to about 130° C., about 130° C. to about 150° C., about 130° C. to about 140° C., or about 140° C. to about 150° C.

The microwave irradiation may be performed for about 30 minutes to about 90 minutes, about 30 minutes to about 80 minutes, about 30 minutes to about 70 minutes, about 30 minutes to about 60 minutes, about 30 minutes to about 50 minutes, about 30 minutes to about 40 minutes, about 40 minutes to about 90 minutes, about 40 minutes to about 80 minutes, about 40 minutes to about 70 minutes, about 40 minutes to about 60 minutes, about 40 minutes to about 50 minutes, about 50 minutes to about 90 minutes, about 50 minutes to about 80 minutes, about 50 minutes to about 70 minutes, about 50 minutes to about 60 minutes, about 60 minutes to about 90 minutes, about 60 minutes to about 80 minutes, about 60 minutes to about 70 minutes, about 70 minutes to about 90 minutes, about 70 minutes to about 80 minutes, or about 80 minutes to about 90 minutes.

The microwave irradiation may be performed under pressure at a temperature of about 110° C. to about 150° C. for about 30 minutes to about 90 minutes. In one or more embodiments, the microwave irradiation may be performed at a pressure of about 2 atm to about 100 atm at a temperature of about 110° C. to about 150° C. for about 30 minutes to about 90 minutes. In one or more embodiments, the microwave irradiation may be performed at a pressure of about 2 atm to about 100 atm at a temperature of about 120° C. to about 150° C. for about 30 minutes to about 90 minutes. T In one or more embodiments, the microwave irradiation may be performed at a temperature of 120° C. to about 150° C. for about 30 minutes to about 90 minute. In one or more embodiments, the microwave irradiation may be performed at pH 5.0 to 7.0, pH 5.0 to 6.0, or neutral pH.

Another aspect of the present disclosure provides an extract of plants in the genus *Panax* produced by the method.

Another aspect of the present disclosure provides a pharmaceutical composition including the extract of plants in the genus *Panax* produced by the method. The pharmaceutical composition may be intended for inhibition of resistance to an anticancer drug, such as Taxol, skin protection, anti-diabetic treatment, anticancer treatment (for example, anti-lung cancer treatment, anti-liver cancer treatment, etc), anti-inflammation, antioxidation, inhibition of platelet aggregation, or improvement of skin. The pharmaceutical composition may further include a pharmaceutically acceptable carrier or diluent.

The extract may include ginsenosides Rg6, Rk3, Rh4 in significantly higher amounts than those in a product of the simple heat treatment, and accordingly, may have enhanced medical effects of ginsenosides Rg6, Rk3, and Rh4. Ginsenoside Rg6 is known to have medicinal effects of inhibition of resistance to an anticancer agent, protection of skin, anti-diabetes, and an anticancer. Ginsenoside Rk3 shows medicinal effects of inhibition of proliferation of lung and liver cancer cell lines, induction of apoptosis, anti-inflammatory activity, and antioxidant activity. Ginsenoside Rh4 is known to have medicinal effects of inhibition of platelet aggregation, anti-inflammatory activity, and protection of skin. Thus, the extract may significantly increase such effects compared to a product of the simple heat treatment.

Another aspect of the present disclosure provides a composition for foods, the composition including the extract of plants in the genus *Panax* produced by the method. The foods may include functional foods or health functional foods. The composition for foods may further a carrier or diluent acceptable as a food.

Another aspect of the present disclosure provides a cosmetic composition for improving skin wrinkles, the cosmetic composition including the extract of plants in the genus *Panax* produced by the method. The cosmetic composition may be prepared in a formulation, for example, lotion, suitable for skin administration.

Hereinafter, the present disclosure will be described in detail with reference to Examples. However, these Examples are provided for illustrative purposes only, and the present disclosure is not limited thereto.

Example 1: Preparation of *Ginseng* Leaf

A ginseng leaf (i.e., *Panax ginseng* leaf) used herein was harvested in July from the areas around Ansan-si, Gyeonggido, Korea. 2 L of 50% ethanol was added to 100 g of finely cut ginseng leaf, and a reflux extraction process was performed under elevated temperature conditions at a temperature of about 80° C. for 2 hours, thereby obtaining an extract of 50% ethanol. The resulting extract of 50% ethanol was dried to evaporate a solvent therefrom under reduced pressure, thereby obtaining 14.5 g of a dried extract including ginsenosides Rg1 and Re at a weight of 55% or more with respect to ginsenosides Rg1, Re, Rb1, Re, Rb2, and Rd.

Examples 2 to 7: Processing of *Ginseng* Leaf Extract Using Microwaves (1)

The extract of 50% ethanol obtained in Example 1 was subjected to a heat treatment process using microwaves. In detail, 200 mg of the ginseng leaf extract was added with 1 mL of 50% ethanol solution to a 10 mL container in a microwave irradiation apparatus (CEM 908005 model, USA). The container was sealed so that the contents of the container were closed from the outside air, and the container was subjected to microwave irradiation under conditions of the irradiation time set to 30 minutes, the microwave power set to 100 W (main frequency of 2,455 MHz), and the irradiation temperature set to 110° C. (Example 2), 120° C. (Example 3), 130° C. (Example 4), 140° C. (Example 5), and 150° C. (Example 6), respectively. Then, a lyophilization process was performed thereon, so as to obtain processed products by the microwave irradiation. Here, the pressure set for the microwave irradiation was 20 atm, and the initial reactant of the microwave irradiation had pH 5.7.

Examples 8 to 13: Processing of *Ginseng* Leaf Extract Using Microwaves (2)

The extract of 50% ethanol obtained in Example 1 was subjected to a heat treatment process using microwaves. In detail, 200 mg of the ginseng leaf extract was added with 1 mL of 50% ethanol solution to a 10 mL container in a microwave irradiation apparatus (CEM 908005 model, USA). The container was sealed, and then subjected to microwave irradiation under conditions of the irradiation temperature set to about 120° C., the microwave power set to 100 W (main frequency of 2,455 MHz), and the irradiation time set to 40 minutes (Examples 7), 50 minutes (Examples 8), 60 minutes (Examples 9), 70 minutes (Examples 10), 80 minutes (Examples 11), and 90 minutes (Examples 12), respectively. Then, a lyophilization process was performed thereon, so as to obtain processed products by the microwave irradiation. Here, the pressure set for the microwave irradiation was 20 atm.

Experimental Example 1: Ginsenoside Analysis of Microwave-Processed Products (1) Protocol Respective saponin components of the processed ginseng leaf extract obtained in the above Example were analyzed based on the verification values using ginsenosides Rg6, Rk3, and Rh4 standards. The saponin analysis was repeated three times to confirm reproducibility. In ultra-performance liquid chromatography (UPLC), Eluent solvent A was water and Eluent solvent B was acetonitrile, and the two pumps were used to pump the two solvents, respectively. Here, by using a syringe, 3 μl of the standard solution was injected to a reversed phase column (C18, 2.1 mm×150 mm) which is a separation column, and an eluent solvent composed of 85 volume % of Eluent solvent A and 15 volume % Eluent solvent B was exuded at a flow rate of 0.5 mL/min. Afterwards, the volume % of Eluent solvent B was gradually changed to 30% (28 minutes), 32% (30 minutes), 38% (36 minutes), 43% (47 minutes), 55% (54 minutes), 70% (70 minutes), and 90% (76 minutes), and such a changed composition was maintained for 6 minutes. Then, the resulting components separated from the column were each analyzed through UV spectroscopy.

(2) Experiment Results

As a result of the experiment, the components separated from the column by performing the UPLC analysis on the processed ginseng leaf extract were each subjected to the UPLC chromatography, and peaks shown in FIGS. 1 to 12 were obtained. In FIG. 1, the horizontal axis represents time (in minutes) and the vertical axis represents an arbitrary unit (AU).

FIG. 1 is a UPLC chromatogram of ginsenoside components of a raw ginseng leaf extract. Hereinafter, the term "raw ginseng leaf extract" refers to a water or 50% ethanol solution extract obtained in Example 1.

Figure 2:
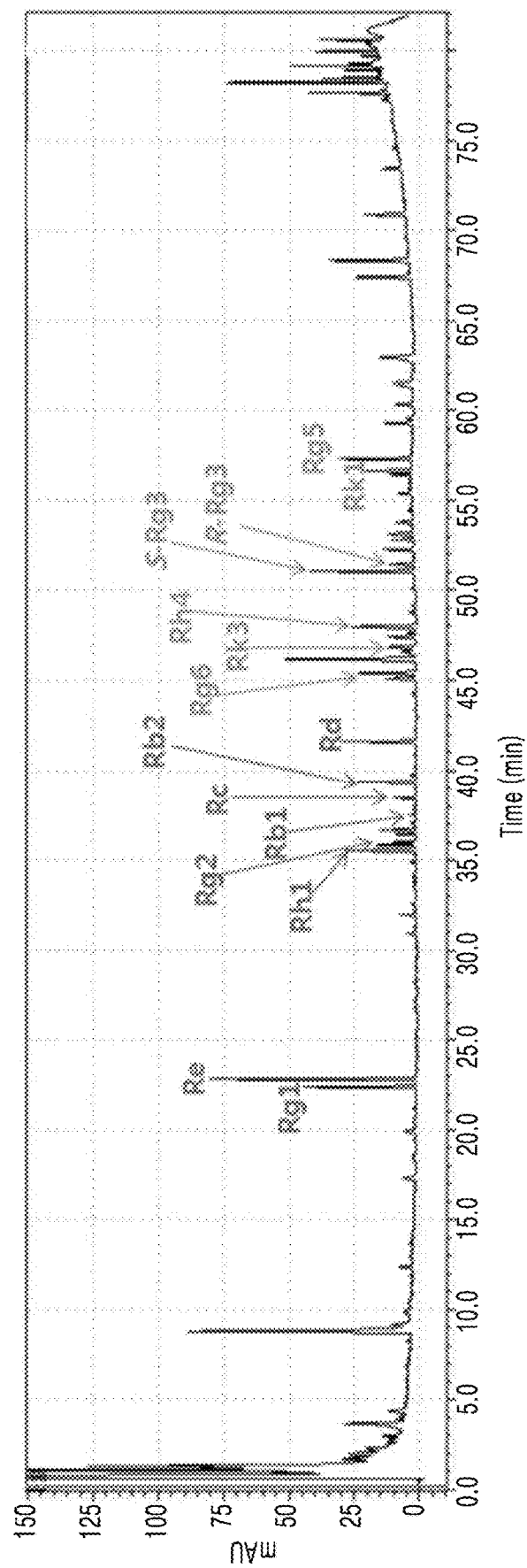
FIG. 2 is a UPLC chromatogram of ginsenoside components in a microwave-processed product obtained by microwave irradiation of a ginseng leaf extract at a temperature of 110° C. for 30 minutes with microwave power set to 100 W.

FIG. 2 is a UPLC chromatogram of ginsenoside components in a microwave-processed product obtained by microwave irradiation of a ginseng leaf extract at a temperature of 110° C. for 30 minutes with microwave power set to 100 W.

Figure 3:
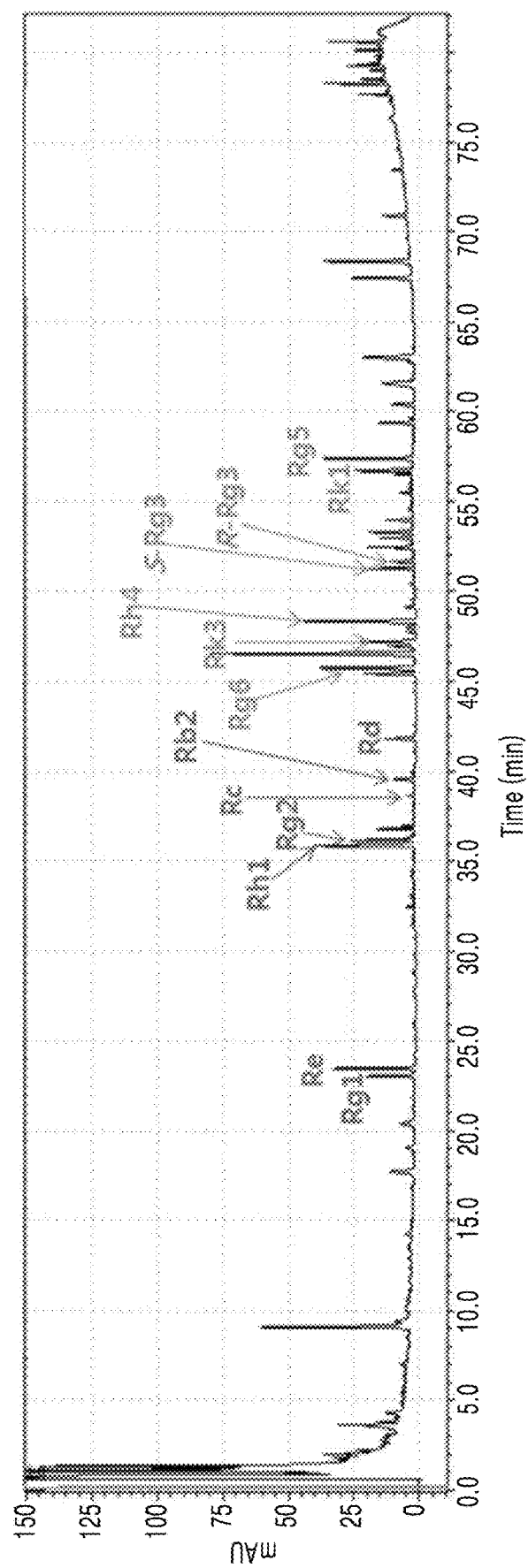
FIG. 3 is a UPLC chromatogram of ginsenoside components in a microwave-processed product obtained by microwave irradiation of a ginseng leaf extract at a temperature of 120° C. for 30 minutes with microwave power set to 100 W.

FIG. 3 is a UPLC chromatogram of ginsenoside components in a microwave-processed product obtained by microwave irradiation of a ginseng leaf extract at a temperature of 120° C. for 30 minutes with microwave power set to 100 W.

Figure 4:
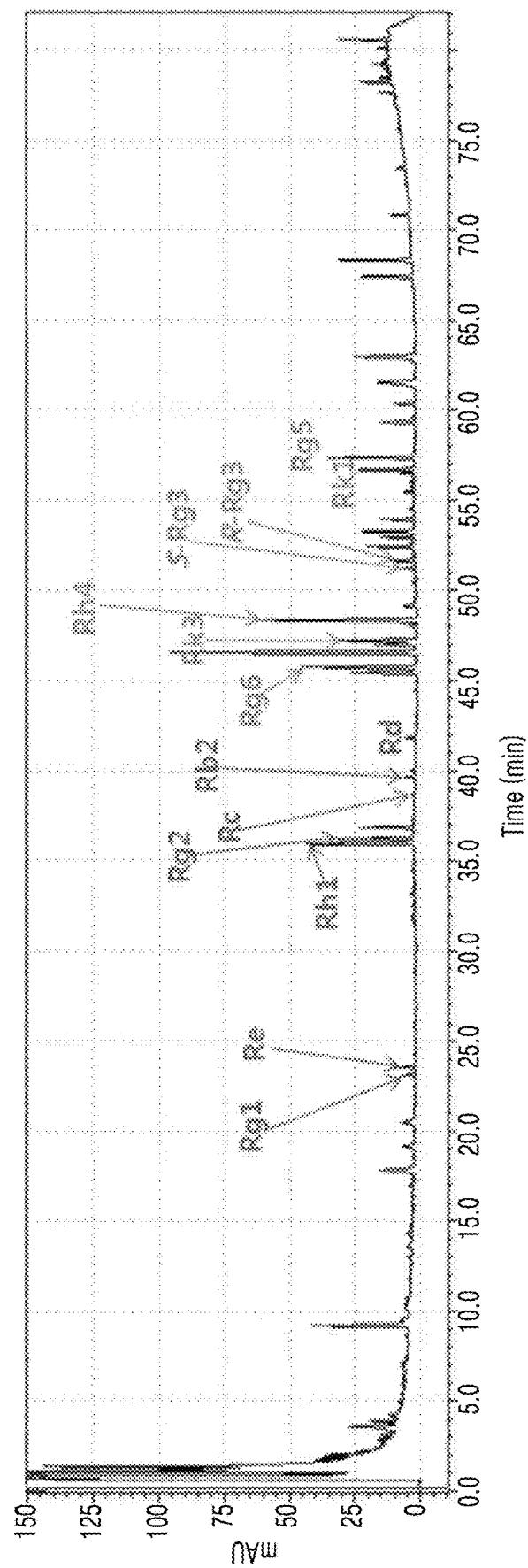
FIG. 4 is a UPLC chromatogram of ginsenoside components in a microwave-processed product obtained by microwave irradiation of a ginseng leaf extract at a temperature of 130° C. for 30 minutes with microwave power set to 100 W.

FIG. 4 is a UPLC chromatogram of ginsenoside components in a microwave-processed product obtained by microwave irradiation of a ginseng leaf extract at a temperature of 130° C. for 30 minutes with microwave power set to 100 W.

Figure 5:
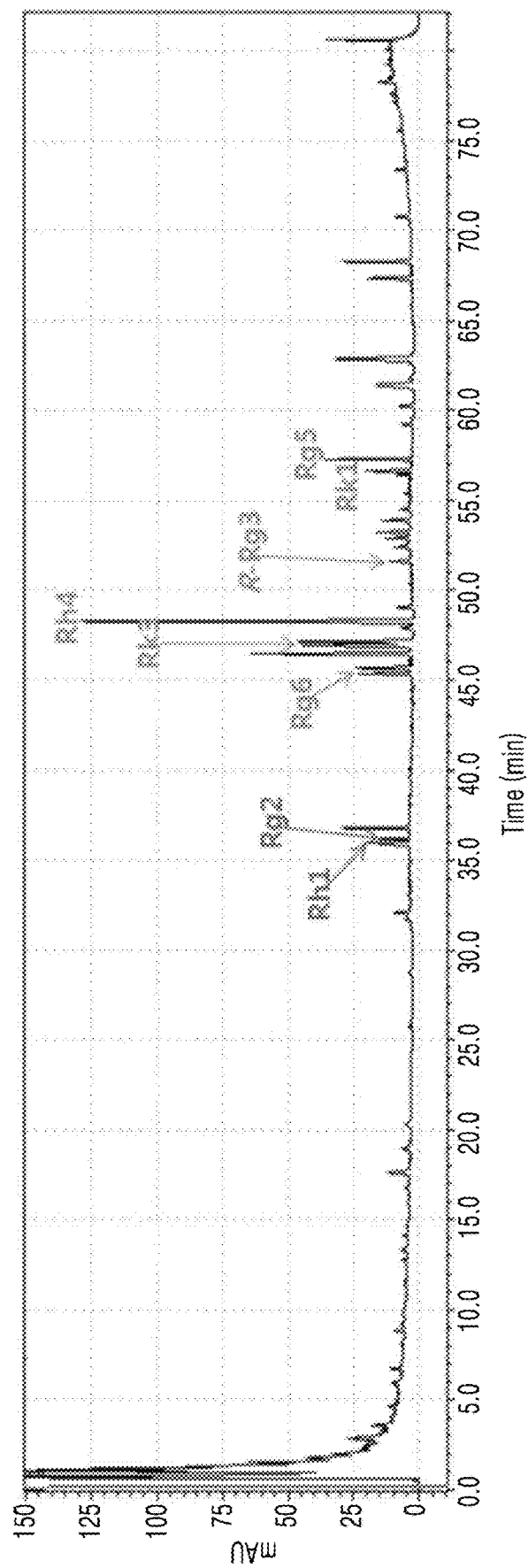
FIG. 5 is a UPLC chromatogram of ginsenoside components in a microwave-processed product obtained by microwave irradiation of a ginseng leaf extract at a temperature of 140° C. for 30 minutes with microwave power set to 100 W.

FIG. 5 is a UPLC chromatogram of ginsenoside components in a microwave-processed product obtained by microwave irradiation of a ginseng leaf extract at a temperature of 140° C. for 30 minutes with microwave power set to 100 W.

Figure 6:
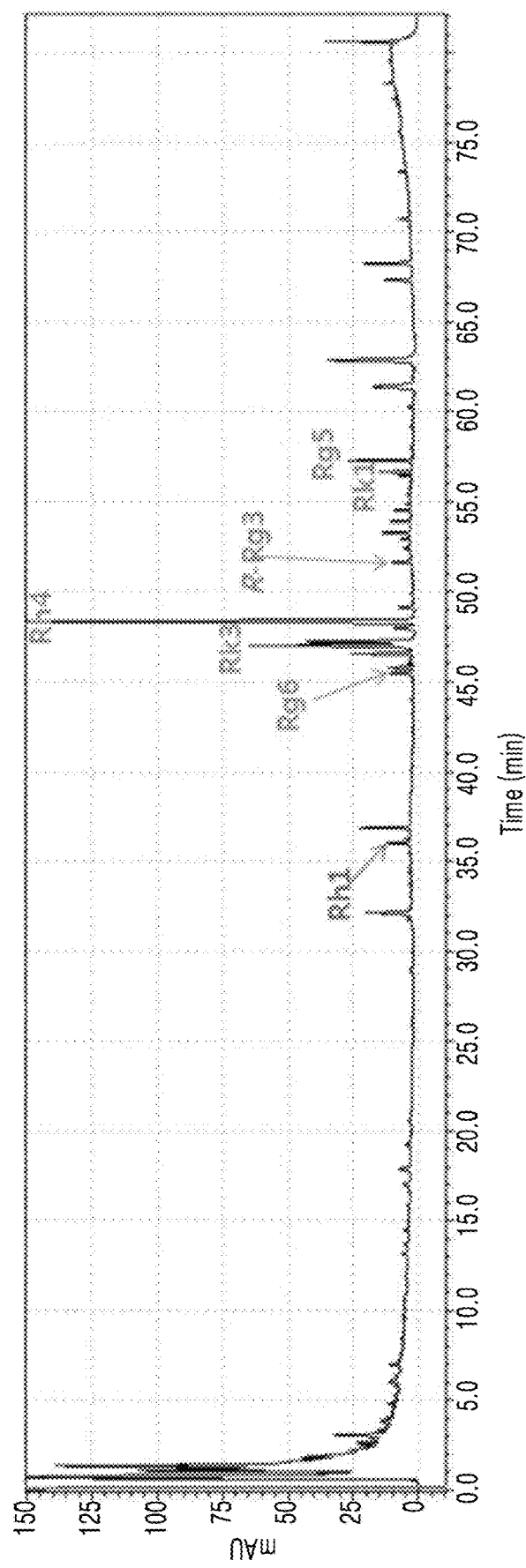
FIG. 6 is a UPLC chromatogram of ginsenoside components in a microwave-processed product obtained by microwave irradiation of a ginseng leaf extract at a temperature of 150° C. for 30 minutes with microwave power set to 100 W.

FIG. 6 is a UPLC chromatogram of ginsenoside components in a microwave-processed product obtained by microwave irradiation of a ginseng leaf extract at a temperature of 150° C. for 30 minutes with microwave power set to 100 W.

Figure 7:
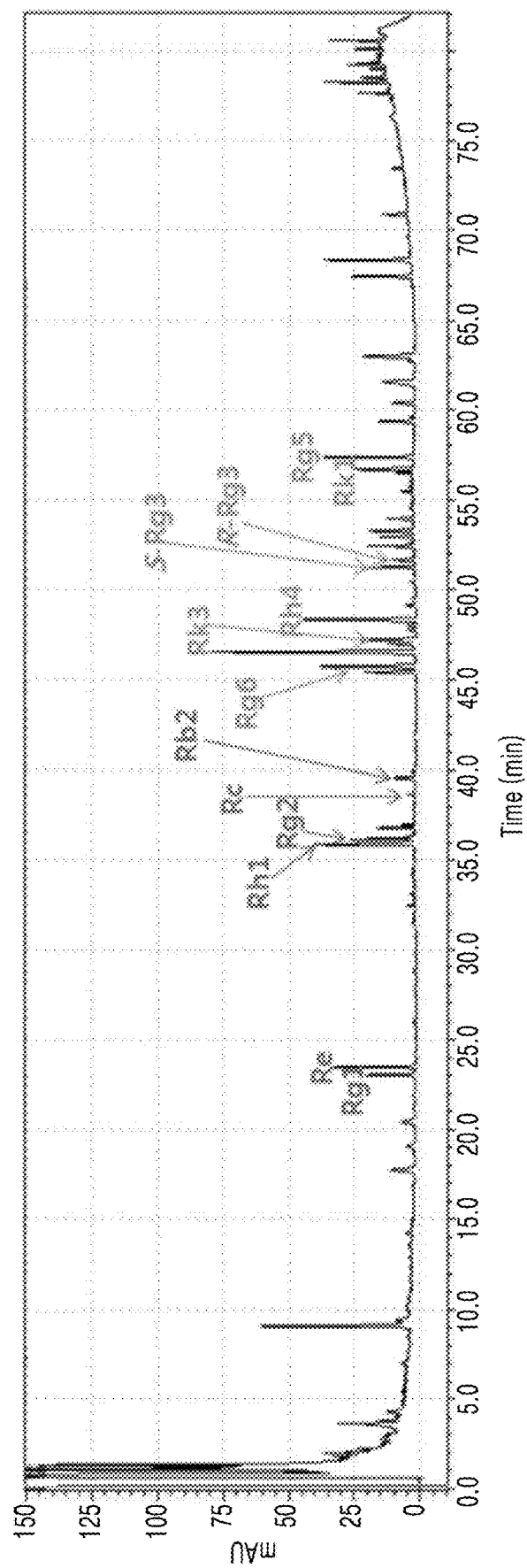
FIG. 7 is a UPLC chromatogram of ginsenoside components in a microwave-processed product obtained by microwave irradiation of a ginseng leaf extract at a temperature of 120° C. for 40 minutes with microwave power set to 100 W.

FIG. 7 is a UPLC chromatogram of ginsenoside components in a microwave-processed product obtained by microwave irradiation of a ginseng leaf extract at a temperature of 120° C. for 40 minutes with microwave power set to 100 W.

Figure 8:
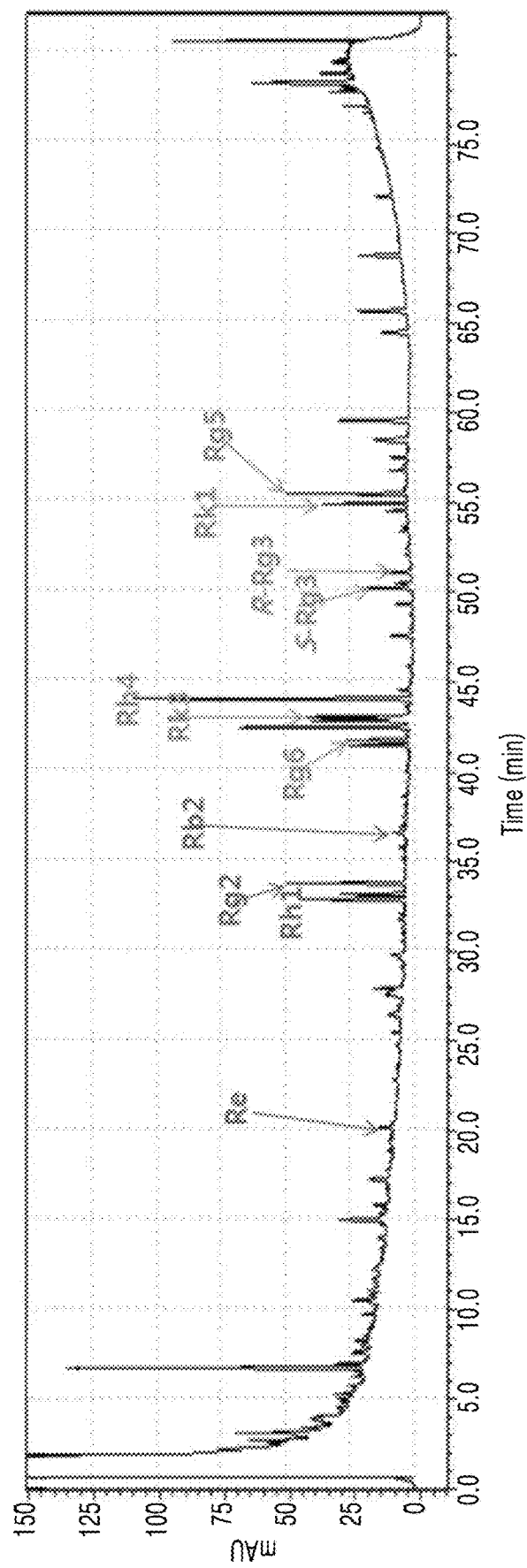
FIG. 8 is a UPLC chromatogram of ginsenoside components in a microwave-processed product obtained by microwave irradiation of a ginseng leaf extract at a temperature of 120° C. for 50 minutes with microwave power set to 100 W.

FIG. 8 is a UPLC chromatogram of ginsenoside components in a microwave-processed product obtained by microwave irradiation of a ginseng leaf extract at a temperature of 120° C. for 50 minutes with microwave power set to 100 W.

Figure 9:
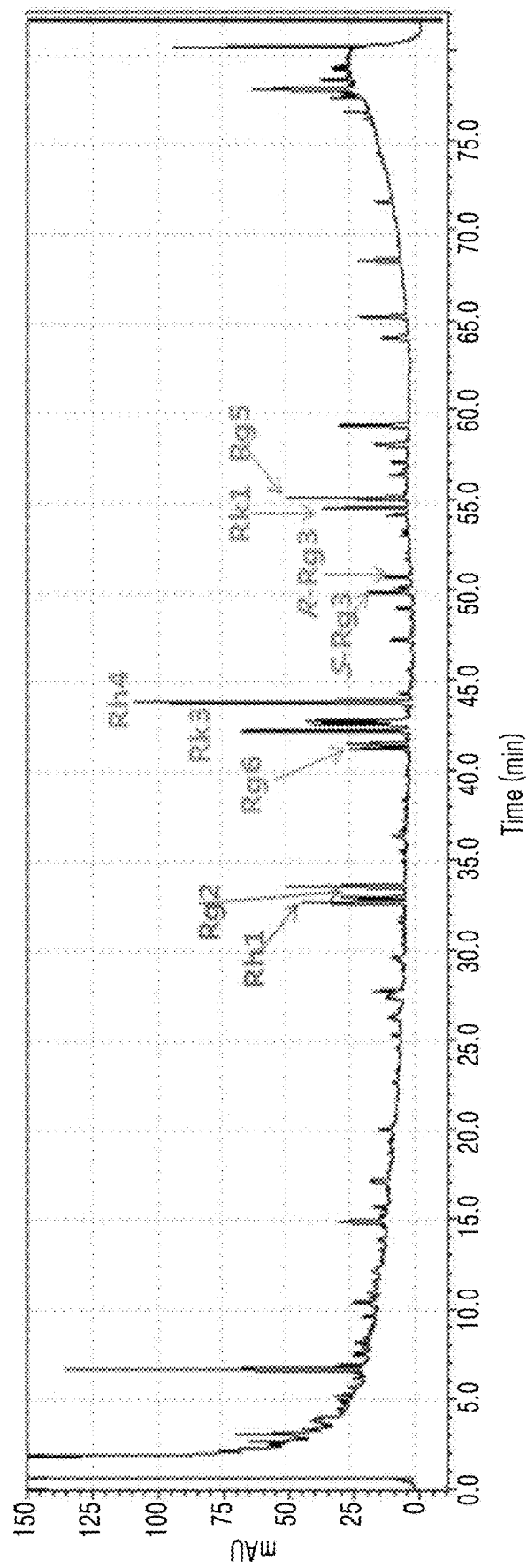
FIG. 9 is a UPLC chromatogram of ginsenoside components in a microwave-processed product obtained by microwave irradiation of a ginseng leaf extract at a temperature of 120° C. for 60 minutes with microwave power set to 100 W.

FIG. 9 is a UPLC chromatogram of ginsenoside components in a microwave-processed product obtained by microwave irradiation of a ginseng leaf extract at a temperature of 120° C. for 60 minutes with microwave power set to 100 W.

Figure 10:
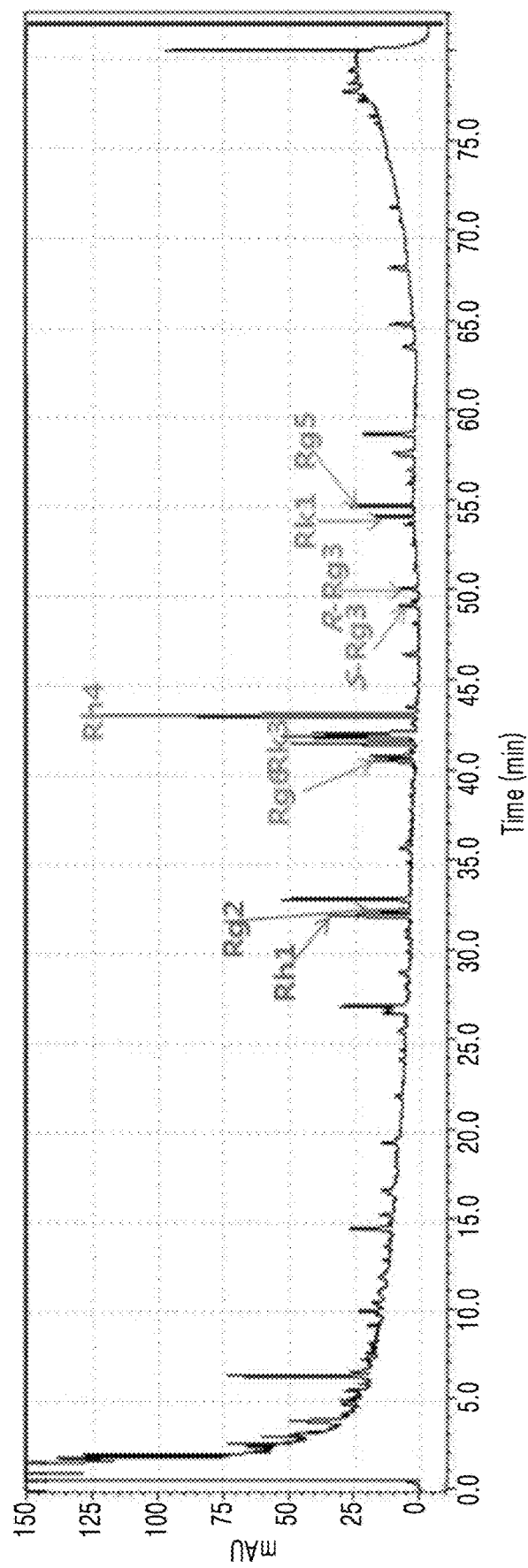
FIG. 10 is a UPLC chromatogram of ginsenoside components in a microwave-processed product obtained by microwave irradiation of a ginseng leaf extract at a temperature of 120° C. for 70 minutes with microwave power set to 100 W.

FIG. 10 is a UPLC chromatogram of ginsenoside components in a microwave-processed product obtained by microwave irradiation of a ginseng leaf extract at a temperature of 120° C. for 70 minutes with microwave power set to 100 W.

Figure 11:
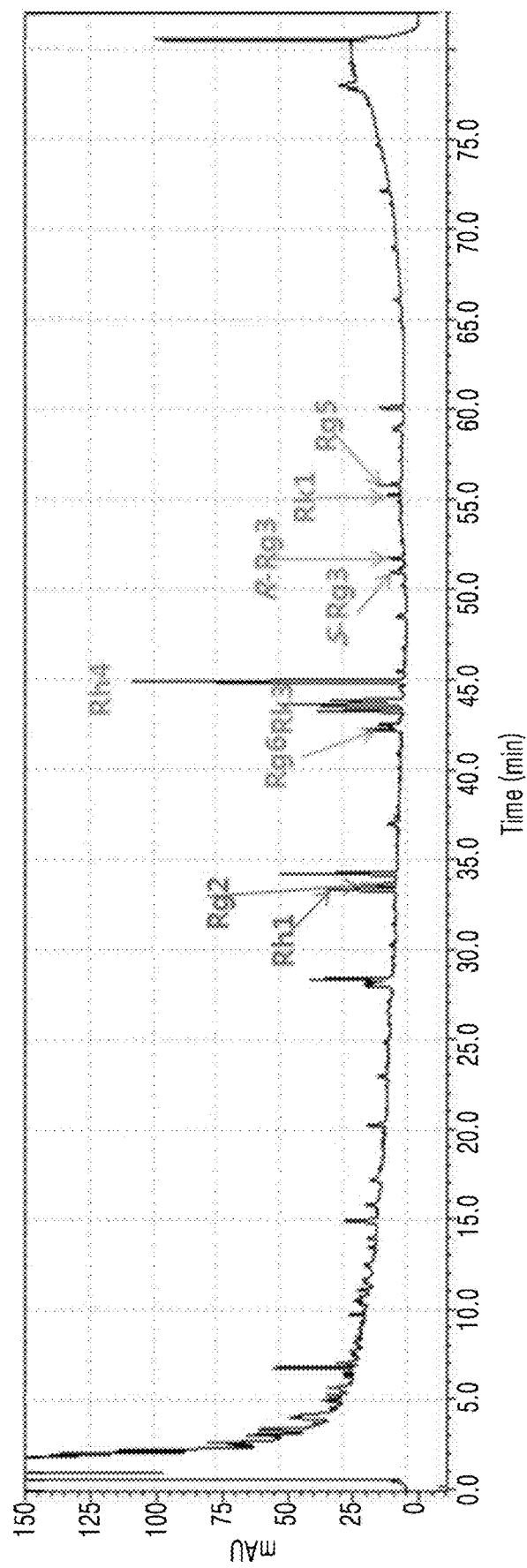
FIG. 11 is a UPLC chromatogram of ginsenoside components in a microwave-processed product obtained by microwave irradiation of a ginseng leaf extract at a temperature of 120° C. for 80 minutes with microwave power set to 100 W.

FIG. 11 is a UPLC chromatogram of ginsenoside components in a microwave-processed product obtained by microwave irradiation of a ginseng leaf extract at a temperature of 120° C. for 80 minutes with microwave power set to 100 W.

Figure 12:
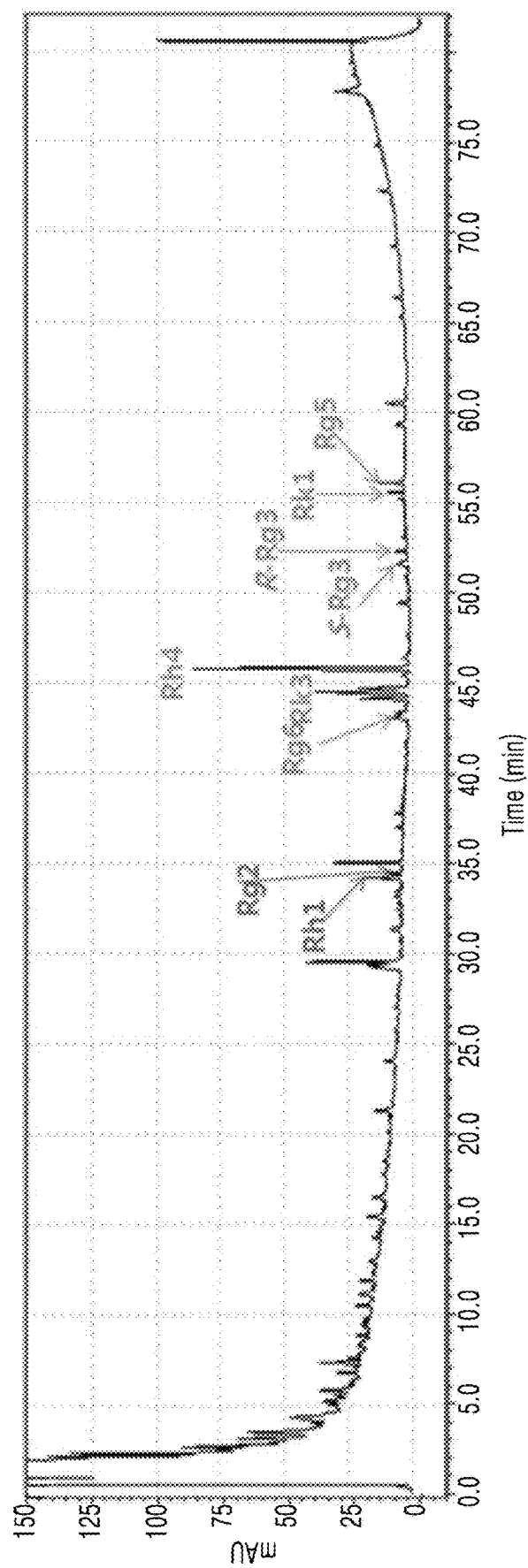
FIG. 12 is a UPLC chromatogram of ginsenoside components in a microwave-processed product obtained by microwave irradiation of a ginseng leaf extract at a temperature of 120° C. for 90 minutes with microwave power set to 100 W.

FIG. 12 is a UPLC chromatogram of ginsenoside components in a microwave-processed product obtained by microwave irradiation of a ginseng leaf extract at a temperature of 120° C. for 90 minutes with microwave power set to 100 W.

In addition, the results of calculating the amounts of each ginsenoside obtained by the UPLC chromatography are summarized in Tables 1 and 2.

TABLE 1

| | Example 1 | Example 2 | Example 3 | Example 4 | Example 5 | Example 6 | Example 7 | Example 8 | Example 9 | Example 10 | Example 11 | Example 12 |
|---|---|---|---|---|---|---|---|---|---|---|---|---|
| Rg1 | 43.5 | 20.6 | 15.4 | 4.1 | — | — | 23.6 | 10.9 | — | — | — | — |
| Re | 52.6 | 24.7 | 19.0 | 5.4 | — | — | — | — | — | — | — | — |
| Rh1 | — | 16.8 | 10.3 | 5.2 | 2.2 | 1.5 | 14.0 | 5.9 | 4.8 | 4.2 | 2.5 | — |
| Rg2 | — | 6.5 | 4.1 | 2.3 | 0.5 | — | 5.4 | 2.4 | 1.5 | 1.2 | 0.9 | — |
| Rb1 | 22.3 | 18.7 | 11.3 | — | — | — | — | — | — | — | — | — |
| Rc | 20.8 | 7.9 | 6.9 | — | — | — | 3.0 | — | — | — | — | — |
| F1 | — | — | — | — | — | — | — | — | — | — | — | — |
| Rb2 | 12.1 | 6.2 | 7.0 | — | — | — | 6.2 | 4.5 | — | — | — | — |
| Rd | 21.0 | 18.8 | 8.8 | — | — | — | — | — | — | — | — | — |
| Rg6 | — | 7.2 | 12.6 | 15.6 | 9.0 | 4.0 | 23.6 | 16.5 | 12.1 | 9.1 | 7.1 | 5.7 |
| Rk3 | — | 3.4 | 10.0 | 13.0 | 21.0 | 24.4 | 20.1 | 26.7 | 22.7 | 19.8 | 15.1 | 11.9 |
| Rh4 | — | 4.6 | 11.5 | 15.2 | 27.6 | 34.8 | 22.3 | 30.0 | 36.3 | 31.0 | 23.3 | 18.2 |
| F2 | — | — | — | — | — | — | — | — | — | — | — | — |
| S-Rg3 | — | 5.1 | 8.6 | 10.1 | 5.5 | 1.7 | 6.1 | 5.2 | 1.9 | 1.3 | 0.6 | 0.4 |
| R-Rg3 | — | 6.9 | 9.6 | 10.5 | 9.0 | 3.3 | 9.0 | 8.5 | 7.1 | 5.9 | 3.1 | 2.1 |
| C-Y | — | — | — | — | — | — | — | — | — | — | — | — |
| C-K | — | — | — | — | — | — | — | — | — | — | — | — |
| Rk1 | — | 8.2 | 7.4 | 8.8 | 8.3 | 6.4 | 7.2 | 7.2 | 4.6 | 2.9 | 1.5 | 1.3 |
| Rg5 | — | 4.9 | 10.8 | 9.9 | 9.9 | 8.1 | 9.0 | 7.7 | 6.1 | 5.9 | 3.3 | — |
| Rh2 | — | — | — | — | — | — | — | — | — | — | — | — |
| Rk2 | — | — | — | — | — | — | — | — | — | — | — | — |
| Rh3 | — | — | — | — | — | — | — | — | — | — | — | — |
| Total | 172.3 | 160.2 | 153.3 | 100.1 | 93.0 | 84.2 | 149.5 | 125.5 | 97.1 | 81.3 | 57.4 | 38.3 |

TABLE 2

| | Amount of the sum of Rg6 + Rk3 + Rh4 based on the total ginsenosides (weight %) |
|---|---|
| Example 1 | 0.0 |
| Example 2 | 9.5 |
| Example 3 | 22.2 |
| Example 4 | 43.8 |
| Example 5 | 61.9 |
| Example 6 | 75.1 |
| Example 7 | 44.2 |
| Example 8 | 58.3 |
| Example 9 | 73.2 |
| Example 10 | 73.7 |
| Example 11 | 79.3 |
| Example 12 | 93.5 |

Table 3 shows weight % of R6, Rk3, and Rh4 based on the total ginsenosides.

TABLE 3

| | Ex 1 | Ex 2 | Ex 3 | Ex 4 | Ex 5 | Ex 6 | Ex 7 | Ex 8 | Ex 9 | Ex 10 | Ex 11 | Ex 12 |
|---|---|---|---|---|---|---|---|---|---|---|---|---|
| Rg6 | 0 | 4.5 | 8.2 | 15.6 | 9.7 | 4.8 | 15.8 | 13.1 | 12.5 | 11.2 | 12.4 | 14.9 |
| Rk3 | 0 | 2.1 | 6.5 | 13.0 | 22.6 | 29.0 | 13.4 | 21.3 | 23.4 | 24.4 | 26.3 | 31.1 |
| Rh4 | 0 | 2.9 | 7.5 | 15.2 | 29.7 | 41.3 | 14.9 | 23.9 | 37.4 | 38.1 | 40.6 | 47.5 |

In Tables 1 and 2, each number represents milligram (mg) of ginsenoside per gram (g) of processed product.

Referring to Examples 2 to 6 in Tables 1 and 2, main ginsenosides Rg1 and/or Re included in the ginseng leaf extract (Example 1) were heat-treated at a temperature in a range of about 120° C. to about 150° C. for 30 minutes, and as a result, it was confirmed that glucose which is glycoside at the 20$^{th}$ position was released, and a dehydration reaction subsequently occurred at the 20$^{th}$ position to be converted into Rg6, Rk3, and Rh4.

Referring to Examples 3 and 7 to 12 in Tables 1 and 2, when the microwave irradiation was performed at a temperature of 120° C. for about 30 minutes to about 90, the amount ratios of ginsenosides Rg6, Rk3, and Rh4 were tended to increase in proportion to the microwave irradiation time.

According to the results above, the ginseng leaf extract was able to more efficiently convert main ginsenosides Rg1 and Re of ginseng to more effective or alternative ginsenosides Rg6, Rk3, and Rh4 by the microwave irradiation. In addition, as shown in Table 2, the microwave-processed products including ginsenosides Rg6, Rk3, and Rh4 at an amount of 9.5% or more, 22.2% or more, or 43.8% or more based on the total ginsenoside weight. In particular, it was confirmed that ginsenosides Rg6, Rk3, and Rh4 were included at an amount that is significantly high compared to the simple heat treatment process developed so far, and this effect is a remarkably unexpected effect compared to the related art.

According to the one or more embodiments, a method of producing an extract of plants in the genus *Panax* may be able to efficiently produce an extract of plants in the genus *Panax* including rare ginsenosides Rg6, Rk3, and Rh4 at a weight of 20% or more with respect to the total ginsenoside weight, wherein the total ginsenoside includes Rg1, Re, Rh1, Rg2, Rb1, Rc, Rb2, Rd, Rg6, Rk3, Rh4, S-Rg3, R-Rg3, Rk1, and Rg5.

According to the one or more embodiments, a pharmaceutical composition including the extract of plants in the genus *Panax* may be used for inhibition of resistance to an anticancer drug, protection of skin, anti-diabetes, anticancer (for example, anti-lung cancer, anti-liver cancer), anti-inflammation, antioxidation, inhibition of platelet aggregation, or improvement of skin wrinkles.

According to the one or more embodiments, a composition for foods including the extract of plants in the genus *Panax* may be used for foods, in particular, functional foods.

According to the one or more embodiments, a cosmetic composition including the extract of plants in the genus *Panax* produced by the method may be used for improvement of skin wrinkles.

It should be understood that embodiments described herein should be considered in a descriptive sense only and not for purposes of limitation. Descriptions of features or aspects within each embodiment should typically be considered as available for other similar features or aspects in other embodiments.

While one or more embodiments have been described with reference to the figures, it will be understood by those of ordinary skill in the art that various changes in form and details may be made therein without departing from the spirit and scope of the disclosure as defined by the following claims.

What is claimed is:

1. A method of producing a *Panax* genus plant extract, the method comprising performing microwave irradiation of leaves of a plant in the genus *Panax* or an extract of the leaves, wherein the *Panax* genus plant extract comprises rare ginsenosides Rg6, Rk3, and Rh4 at a weight of 20% or more with respect to the weight of total ginsenosides obtained, and the total ginsenosides comprise Rg1, Re, Rh1, Rg2, Rb1, Rc, Rb2, Rd, Rg6, Rk3, Rh4, S-Rg3, R-Rg3, Rk1, and Rg5, wherein the microwave irradiation is performed at a pressure of 2 atm to 100 atm, at a temperature of 110° C. to 130° C., for 50 minutes to 90 minutes, and at a pH of 5.0 to 6.0.

2. The method of claim 1, wherein, in reference to the leaves of a plant in the genus *Panax* or the extract of the leaves, the extract of the leaves comprises ginsenosides Rg1 and Re at a weight of 55% or more with respect to the weight of total ginsenosides.

3. The method of claim 1, wherein, in reference to the leaves of a plant in the genus *Panax* or the extract of the leaves, the extract of the leaves is an extract of the leaves of a plant in the genus *Panax* obtained by extraction with water, a $C_1$-$C_6$ alcohol, or a mixture thereof.

4. The method of claim 1, wherein the plant in the genus *Panax* comprises *Panax ginseng, Panax quinquefolius, Panax notoginseng, Panax japonica, Panax Panax pseudoginseng, Panax vietnamensis*, or a combination thereof.

5. The method of claim 1, wherein the microwave irradiation is performed on the leaves of a plant in the genus *Panax* or the extract of the leaves, contained in water, a $C_1$-$C_6$ alcohol, or a mixed solution of water and a $C_1$-$C_6$ alcohol.

* * * * *